US012805709B2

(12) United States Patent
Busch et al.

(10) Patent No.: US 12,805,709 B2
(45) Date of Patent: Nov. 24, 2026

(54) ENDOSCOPE WITH A SUCTION VALVE HAVING A FIXATION RING

(71) Applicant: AMBU A/S, Ballerup (DK)

(72) Inventors: David Busch, Weyarn (DE); Werner Schwarz, Ruhpolding (DE)

(73) Assignee: AMBU A/S, Ballerup (DK)

( * ) Notice: Subject to any disclaimer, the term of this patent is extended or adjusted under 35 U.S.C. 154(b) by 652 days.

(21) Appl. No.: 18/035,065

(22) PCT Filed: Oct. 21, 2021

(86) PCT No.: PCT/EP2021/079276
§ 371 (c)(1),
(2) Date: May 2, 2023

(87) PCT Pub. No.: WO2022/096282
PCT Pub. Date: May 12, 2022

(65) Prior Publication Data
US 2023/0404377 A1 Dec. 21, 2023

(30) Foreign Application Priority Data
Nov. 5, 2020 (DE) ..................... 10 2020 129 207.4

(51) Int. Cl.
*A61B 1/015* (2006.01)
*A61B 1/00* (2006.01)
*A61B 1/05* (2006.01)

(52) U.S. Cl.
CPC .......... *A61B 1/015* (2013.01); *A61B 1/00068* (2013.01); *A61B 1/00045* (2013.01); *A61B 1/05* (2013.01)

(58) Field of Classification Search
CPC ..... A61B 1/012; A61B 1/015; A61B 1/00094; A61B 1/126; A61B 1/127; A61B 1/00066; A61B 1/00068; A61M 1/77; A61M 1/774
See application file for complete search history.

(56) References Cited

U.S. PATENT DOCUMENTS 4,261,343 A * 4/1981 Ouchi ...................... A61B 1/12 600/158
4,270,525 A * 6/1981 Furihata ................. A61M 1/76 600/154
(Continued)

FOREIGN PATENT DOCUMENTS

DE 196 10 312 A1 9/1996
EP 2645921 B1 6/2019
(Continued)

OTHER PUBLICATIONS

International Search Report and Written Opinion in International Application PCT/EP2021/079276, dated Feb. 1, 2022.
(Continued)

*Primary Examiner* — Ryan N Henderson
(74) *Attorney, Agent, or Firm* — Faegre Drinker Biddle & Reath LLP

(57) ABSTRACT

An endoscope including a handle, a distal tip unit, an endoscope shaft connecting the handle and the distal tip unit, a working channel provided in the endoscope shaft and extending from the endoscope handle towards the distal tip unit, and a suction valve configured to control a suction through the working channel and having a valve closed state and a valve open state. The suction valve includes: a housing having an inlet opening connected to the working channel and an outlet opening; and a piston unit inserted in the housing and including a movable piston, a button attached to the piston, a fixation ring arranged stationary in the housing
(Continued)

and a spring arranged and acting between the fixation ring and the button or piston. The fixation ring is configured to urge the piston towards the inlet opening of the housing in the valve closed state.

19 Claims, 4 Drawing Sheets

(56) References Cited

U.S. PATENT DOCUMENTS

| | | | | |
|---|---|---|---|---|
| 4,325,362 | A * | 4/1982 | Ouchi | A61B 1/12 600/158 |
| 4,537,182 | A * | 8/1985 | Otani | A61B 1/00068 251/325 |
| 5,840,015 | A * | 11/1998 | Ogino | A61M 1/7413 600/156 |
| 5,871,441 | A * | 2/1999 | Ishiguro | A61B 1/122 600/159 |
| 6,849,043 | B2 | 2/2005 | Kondo | |
| 6,908,429 | B2 | 6/2005 | Heimberger | |
| 8,568,303 | B2 | 10/2013 | Yamane | |
| 9,585,545 | B2 | 3/2017 | Anderson et al. | |
| 10,271,717 | B2 | 4/2019 | Sueyasu | |
| 10,314,466 | B2 | 6/2019 | Ando | |
| 10,898,062 | B2 | 1/2021 | Wolfe | |
| 2003/0181787 | A1* | 9/2003 | Kondo | A61B 1/00068 600/156 |
| 2006/0241348 | A1* | 10/2006 | Kohno | A61B 1/00068 600/158 |
| 2011/0208003 | A1 | 8/2011 | Yamane | |
| 2012/0071844 | A1 | 3/2012 | Yamane | |
| 2012/0088975 | A1* | 4/2012 | Morimoto | A61B 1/00068 600/159 |
| 2013/0338442 | A1 | 12/2013 | Anderson et al. | |
| 2015/0148608 | A1 | 5/2015 | Fukushima et al. | |
| 2015/0216393 | A1* | 8/2015 | Toyoda | A61B 1/00068 600/159 |
| 2015/0216394 | A1* | 8/2015 | Toyoda | F16K 11/0716 600/131 |
| 2017/0087263 | A1 | 3/2017 | Sato | |
| 2017/0290495 | A1 | 10/2017 | Ando | |
| 2017/0347860 | A1 | 12/2017 | Still et al. | |

FOREIGN PATENT DOCUMENTS

| | | | |
|---|---|---|---|
| JP | 2004-135890 | A | 5/2004 |
| JP | 4185345 | B2 | 11/2008 |
| JP | 2012-065767 | A | 4/2012 |
| JP | 2012-071023 | A | 4/2012 |
| JP | 2015-146926 | A | 8/2015 |

OTHER PUBLICATIONS

Search Report from German patent application No. 10 2020 129 207.4, dated Aug. 6, 2021.

* cited by examiner

ENDOSCOPE WITH A SUCTION VALVE HAVING A FIXATION RING

CROSS REFERENCE TO RELATED APPLICATIONS

This application is a National Phase entry under 35 U.S.C. § 371 of International Application No. PCT/EP2021/079276, filed Oct. 21, 2021, which claims the benefit of and priority from German Patent Application No. DE 10 2020 129 207.4, filed Nov. 5, 2020; said applications are incorporated by reference herein in their entirety.

The present disclosure relates to an endoscope comprising a proximal endoscope handle, a distal tip unit configured to be inserted into a patient's body cavity, an endoscope shaft connecting the endoscope handle and the distal tip unit, a working channel provided in the endoscope shaft and extending from the endoscope handle towards the distal tip unit and a suction valve configured to control a suction through the working channel and having a valve closed state and a valve open state. The suction valve comprises: a housing having an inlet opening connected to the working channel and an outlet opening; and a piston unit inserted in the housing. The piston unit comprises a movable piston, a button attached to the piston, a fixation ring arranged stationary in the housing and a spring arranged and acting between the fixation ring and the button or piston.

PRIOR ART

Endoscopes and similar specialized instruments such as bronchoscopes, arthroscopes, colonoscopes, laparoscopes and duodenoscopes are well known from the state of the art and are used for visual examination and diagnosis of hollow organs and body cavities, as well as to assist in surgery, e.g. for a targeted tissue sampling. Basically, a distal tip unit of an endoscope, which is connected to an endoscope handle via an endoscope shaft, can be inserted into a hollow organ or body cavity to be investigated with the endoscope. Both reusable and disposable endoscopes are known from the state of the art.

When examining an object such as a body cavity or hollow organ with an endoscope it is desirable to have a clear view/visibility of the examined object. However, the visibility of such an object is often affected by mucus or other undesirable fluid content. It is thus desirable to remove such mucus or undesirable fluid content using a suction device, such as a vacuum pump. In order to connect the suction device to the endoscope and to control a suction that shall be applied to the examined object, it is basically known to use/provide a suction valve.

For example, a suction valve for an endoscope may be connected to a working channel of the endoscope and may be configured to allow or prevent a suction/suction effect in the working channel. When the suction valve is in a valve closed position (i.e. a closed position of the suction valve), a fluid/air flow through the working channel is blocked by the suction valve. When suction is desired in the working channel, an operator/a user can (manually) operate the suction valve (e.g. by depressing a button of the valve) in order to bring the suction valve in a valve open position (i.e. an open position of the suction valve). In the open position of the suction valve a flow channel inside the suction valve connects the working channel to the suction device. In particular, the suction device creates a negative (suction) pressure that draws fluid/air out of the working channel and out of an outlet opening provided in the suction valve. When the operator releases the suction valve (e.g. by not depressing the button anymore), the valve returns to its valve closed position that prohibits fluid/air flow and ends the suctioning out of the working channel. Often, the suction valve is removable from the endoscope/an endoscope handle so that potential blockage of the valve can be removed.

Basically, suction valves comprising a housing and a piston that is movable within the housing are well-known.

For example, U.S. Pat. No. 5,871,441 A discloses a suction valve that can be connected to a working channel of an endoscope and includes a (cylindrical) housing, a piston, a spring and a button. The piston is provided with a flow channel and is movably accommodated within the housing. The button (on top of the piston) is connected to the piston such that the piston is movable together with the button. An operator can press the button to move the piston from a valve closed state to a valve open state. The spring ensures that the valve is usually in the valve closed state, in particular when the operator does not press down the button. The housing is provided with an inlet opening that is connected to the working channel of the endoscope and with an outlet opening that is connected to a suction device. Usually, the suction device is active/running. When the valve is in the valve closed state an outer circumferential surface of the cylindrically shaped piston blocks the inlet opening. When the operator presses down the button, the piston is moved downwards such that the flow channel of the piston connects the inlet opening of the housing with the outlet opening of the housing, and a fluid flow through the suction valve is enabled. Hence, fluid/air can be drawn from the working channel of the endoscope through the suction valve.

DE 196 10 312 A1 discloses a suction valve that is assembled in a similar way as the suction valve disclosed in U.S. Pat. No. 5,871,441 A.

Usually, for reusable endoscopes suction valves are used that generally comprise metal parts. Metal parts can be manufactured with high precision and the valves can include proper sealings that ensure a good performance of the suction valves. However, for single use endoscopes/disposable endoscopes this solution is too expensive and resource-demanding. For single use endoscopes it is thus preferable to provide a suction valve which is essentially produced/manufactured of plastic/polymer/synthetic material. Plastic parts however cannot be produced as accurately as metal parts. In particular, for plastic parts tolerances are bigger than for metal parts. Furthermore, surfaces of molded plastic parts are usually slightly tapered (in order to allow removal of a mold/a mold core) which leads to challenges ensuring a proper sealing of the valve.

In particular, suction valves essentially made of plastic parts have the drawback that residual suction from the working channel (entering the suction valve over the inlet opening) occurs in the valve closed state. Therefore, it is necessary to improve a sealing of the inlet opening in the valve closed state. As for disposable endoscopes/suction valves for disposable endoscopes usually (molded) plastic parts are used, the sealing between two surfaces cannot be easily achieved by a flat contact of these surfaces. Hence, additional sealing (means) should be provided to reduce/eliminate the residual flow.

Against this background, EP 2 645 921 B1 discloses a disposable suction valve for an endoscope with a stem (piston) providing an air passage through a center bore. Furthermore, the suction valve includes a spring stanchion cup and a spring as well as a boot that is placed over the exterior of the spring stanchion cup. The spring stanchion cup comprises an opening to receive the stem and to allow movement of the stem between an upward and a downward position. The spring is placed between the spring stanchion cup and the stem. A separate/additional sealing ledge is provided at the spring stanchion cup to seal off a suction port in the endoscope.

A major drawback of the existing solutions is that an additional and/or separate seal is necessary to reduce/eliminate the residual suction.

BRIEF DESCRIPTION OF THE DISCLOSURE

The tasks and objectives of the present disclosure are to eliminate or at least to reduce the disadvantages of the prior art. In particular, a suction valve shall be provided that at least reduces, preferably eliminates, the residual suction through the suction valve without additional and/or separate seals. When providing a suction valve with less individual parts, the assembly of such suction valve can be eased and the costs of such suction valve can be reduced.

The tasks and objectives are solved by an endoscope in accordance with claim 1 and by a system in accordance with claim 13. Advantageous embodiments are claimed in the dependent claims and/or are explained below.

The present disclosure relates to an endoscope, preferably a single use endoscope, that comprises a proximal endoscope handle, a distal tip unit configured to be inserted into a patient's body cavity, an endoscope shaft connecting the endoscope handle and the distal tip unit, a working channel provided in the endoscope shaft and extending from the endoscope handle towards the distal tip unit and a suction valve configured to control a suction through the working channel and having a valve closed state and a valve open state. The suction valve comprises: a housing having an inlet opening connected to the working channel and an outlet opening; and a piston unit inserted in the housing. The piston unit comprises a movable piston, a button attached to the piston, a fixation ring arranged stationary/immovable in the housing and a spring arranged and acting between the fixation ring and the button or piston. The fixation ring is configured to urge the piston towards the inlet opening of the housing in the valve closed state.

In other words, the present disclosure provides a suction valve having, inter alia, a fixation ring and a piston, the fixation ring and the piston working together to seal/close the inlet opening of the housing in a valve closed state. In particular, in the valve closed state a peripheral/circumferential portion of the piston is urged/pressed towards/against the inlet opening of the housing by the fixation ring.

Advantageously, the set-up/the assembly of the suction valve according to the disclosure uses the piston and fixation ring which are configured in a way that they can interact in order to provide a better sealing against undesired residual suction entering the suction valve via the inlet opening in the valve closed state. This renders any further separate and/or additional seals for sealing the inlet opening against residual suction in the valve closed state unnecessary. As according to the present disclosure no further additional and/or separate seals are necessary for the suction valve, the assembly of the suction valve is simplified and the production costs of the suction valve are reduced.

The suction valve, in particular the parts thereof, may be made of a plastic material/polymer. Especially preferred, the suction valve, in particular parts thereof, preferably the housing, the piston, the button and the fixation ring, may be manufactured in an injection molding process/may be injection molded parts.

Preferably, the housing and/or the piston and/or the fixation ring and/or the button are made from a thermoplastic polymer, e.g. polystyrene (PS), polycarbonate (PC), acrylonitrile butadiene styrene (ABS), polyoxymethylene (POM), etc. However, also other polymer materials/other materials are conceivable. In particular, it may be preferred if the fixation ring is made from a metal, e.g. stainless steel.

Especially preferred, at least two different (polymer) materials are used for the housing, the piston and the fixation ring. Using two or three different material, in particular polymer materials, for the housing, the piston and the fixation ring helps to reduce friction between these parts.

The housing of the suction valve may be formed essentially cylindrically. In this way, the housing is easy to handle and to manufacture.

Preferably, the spring is configured to urge the suction valve into the valve closed state when no external force, e.g. a pressing force by a user, acts on the button. Hence, when no external force acts on the button, the suction valve is preferably in the valve closed state. In a preferred way, the suction valve is configured such that it is brought into the valve open state when the button is pressed by a user (i.e. when an external pressing force acts on the button). For this purpose, the piston may be movable together with the button.

Moreover, the piston may be configured to seal the inlet opening in the valve closed state, and the piston may be configured to enable a fluid flow between the inlet opening and the outlet opening of the housing in the valve open state.

In a preferred embodiment, the outlet opening of the housing is configured to be connected/to be connectable to a suction device, in particular a vacuum pump. Usually such suction devices are running continuously, no matter if the valve is closed or open. In this way, the suction device may permanently exert suction to the suction valve.

Against this background, the suction valve may be configured such that suction from the working channel is performed (only) in the valve open state. In the valve closed state, a negligibly small, preferably no (residual) suction from the working channel may be suctioned through the suction valve.

Moreover, the suction valve may be configured to manually control the suction through the working channel, in particular by pressing the button towards the housing by a user. In this way, a user can easily control the suction valve and can switch between the valve closed state and the valve open state.

Furthermore, it may be preferred when the suction valve is configured to be removably attachable to the endoscope, in particular to the endoscope handle. In this way, when the suction valve can easily be removed from the endoscope/the endoscope handle, the suction valve can be easily cleaned.

In a further preferred embodiment of the suction valve, the inlet opening is connected to the working channel of the endoscope via a suction tube. In this way, an optimal coupling between the suction valve and the working channel of the endoscope can be ensured.

Moreover, the suction tube ensures to minimize suction losses between (the inlet opening of) the suction valve and the working channel of the endoscope. There may also be a biopsy connector having a biopsy valve be arranged between the suction tube and the working channel. Anyway, it is preferred if there is not a direct connection between the inlet opening and the working channel.

The button may comprise a round button cover portion and a cylindrical button shell portion extending from the button cover portion. This constitutes an easy-to-manufacture design of the button.

Preferably, the button is configured to snap to the housing, in particular to make a snap connection with the housing. In this way, it is very easy to connect the button to the housing.

Moreover, the button may be configured to limit a movement of the piston when the spring urges the button or the piston into the valve closed state. In this way, the button does not part from the housing unintentionally.

Preferentially, the button may be provided with at least one slit, preferably several slits, that allow(s) a leakage flow in the valve closed state. A leakage flow is the drawing in of surrounding air through slit(s) in the button. By providing the button with such slit(s), surrounding air is suctioned through the suction valve and hence the residual suction entering the suction valve over the inlet opening can be reduced or even eliminated. Leakage flow further reduces or even eliminates the risk of excessive initial suction when opening the valve.

The leakage slit(s) may be provided in the button shell portion. Furthermore, the leakage slit(s) may have an elongated slotted shape. Preferably, a plurality of circumferentially (equidistantly) spaced apart leakage slit(s) are provided in the button shell portion. With such a design, the button is configured to provide an appropriate leakage flow through the suction valve in the valve closed state to reduce or even eliminate the residual suction through the inlet opening.

The button may further be provided with an inwardly protruding portion protruding inwardly from the button cover portion wherein the inwardly protruding portion may be configured to snap onto the piston. Against this background, the piston may be provided with a holding arrangement configured to be complementary with the inwardly protruding portion of the button. In this way, the piston can easily be fixed to the button (in a snap-fit manner), in order to be movable with the button.

Furthermore, the fixation ring may be configured to assist in sealing the piston in the valve closed state (when the valve is closed). When the fixation ring urges the piston against the inlet opening, the piston seals the inlet opening against (residual) suction in the valve closed state. This is an easy way to seal the inlet opening without having to provide an additional and/or separate sealing.

In a preferred embodiment, the fixation ring has a ring-shaped/annular/circular portion and a protruding portion, extending along the piston/extending axially away from the ring-shaped portion. Preferably, at least an end portion of the protruding portion is brought into contact with the piston at least in the valve closed state to urge the piston towards/against the inlet opening of the housing.

Preferably, the protruding portion, in particular at least an end portion thereof, is arranged diametrically opposed with respect to the inlet opening of the housing. This results in that the urging effect of the fixation ring onto the piston against the inlet opening is optimal.

Additionally, the piston may have a first (side) opening, a second (bottom) opening and a flow channel enabling fluid flow between the first opening and the second opening.

In the valve open state the first (side) opening, the second (bottom) opening and the flow channel of the piston may connect the inlet opening of the housing with the outlet opening of the housing. Hence, when the piston is arranged appropriately within the housing in the valve open state, the piston allows a fluid flow between the inlet opening and the outlet opening. For this purpose, in the valve open state, the first opening of the piston should be in flush contact with the inlet opening of the housing.

Moreover, the piston may comprise a first (upper) piston portion, a second (lower) piston portion and a transition area between the first piston portion and the second piston portion.

The first piston portion may be a portion of the piston that is fixed to the button (at a free end of the first piston portion), wherein the second piston portion may be a portion of the piston having the first opening, the second opening and the flow channel.

The piston may have an essentially cylindrical shape and the fixation ring, in particular the ring-shaped/annular/circular portion thereof, may encircle/enclose/surround the piston, in particular the first (upper) piston portion. In this way, the fixation ring can easily be coupled with the piston while the piston is movable relative to the fixation ring.

The fixation ring may be fixed to the housing, e.g. frictionally connected or positively connected (form-fit), when the piston unit is installed in the housing.

Furthermore, the piston may have a radially outwardly protruding rim portion in the transition area between the first piston portion and the second piston portion, wherein the radially outwardly protruding rim portion may be urged against the fixation ring by the spring in the valve closed state. Thus, this radially outwardly protruding rim portion functions as an abutment of the piston against the fixation ring in the valve closed state.

In a preferred embodiment, the protruding portion extends from the annular/cylindrical/ring-shaped portion towards and along the second piston portion in an axial direction of the piston.

Preferably, the second piston portion has an axially extending (essentially cylindrical) shell portion which may be interrupted by/provided with a planar surface that extends in a length direction of the piston. This planar surface may be configured to contact the inlet opening of the housing. The planar surface may provide the first opening configured to be flush with the inlet opening of the housing in the valve open state. When the piston is provided with a planar surface at the position where the piston contacts the inlet opening of the housing and when the inner surface of the housing is provided with a correspondingly flat surface at a position around/next to the inlet opening, in the valve closed state these planar surfaces very effectively improve the sealing between the piston and the inlet opening. In the valve open, state this planar surface very effectively allows a flushing coupling between the first opening and the inlet opening such that suction losses can be minimized.

The urging effect of the fixation ring that urges/presses the piston towards the inlet opening of the housing can be embodied in at least two ways. The first and second embodiment described hereinafter can either be used independently from each other or can be combined with one another.

A first embodiment that achieves the urging effect, relates thereto that the protruding portion is designed as a spring-type finger, urging the piston towards the inlet opening by a spring force. In this way, a common piston can be used because simply the spring force of the protruding portion urges the piston against the inlet opening in order to provide the sealing effect. Preferably, the spring-type finger is configured as a leaf spring. Such leaf springs are cheap and easy to handle.

Basically, it may be preferred if the fixation ring is made of an inexpensive polymer material in the first embodiment. In order to increase a shelf life of the spring-type finger it may however be also preferred if the fixation ring is made of a metal, in particular stainless steel, in the first embodiment.

A second embodiment that achieves the urging effect, may be directed thereto that the second piston portion has, besides the axially extending (essentially cylindrical) shell portion, an inclined portion integrally connected/formed at an end of the axially extending (cylindrical) shell portion, wherein in the inclined portion an outer diameter/radius/extension of the piston gradually/continuously/linearly increases from the axially extending shell portion, and wherein the protruding portion of the fixation ring is formed like a wedge and engages at least with the inclined portion in the valve closed state, thus urging the inclined portion towards/in direction of the inlet opening of the housing. In this embodiment, the protruding portion of the fixation ring that is formed like a wedge contacts the inclined portion and hence presses the piston against the inlet opening. Thereby the piston seals the inlet opening against undesired (residual) suction.

Moreover, an obtuse angle (an angle between 90° and 180°) may be formed between the axially extending shell portion and the inclined portion.

Additionally, in the second embodiment, the second piston portion may have a radially outwardly protruding flange portion at an (free) end of the second piston portion while the inclined portion is arranged between the axially extending shell portion and the radially outwardly protruding flange portion, wherein in the inclined portion an outer diameter/radius/ extension of the piston gradually/continuously/linearly increases from the axially extending shell portion to the radially outwardly protruding flange portion. The herewith provided flange portion ensures a strong and safe engagement of the wedge-like protruding portion with the inclined portion.

This second embodiment achieves that the urging effect is very robust and insensitive to long storage.

Furthermore, the present disclosure relates to a system comprising the endoscope described before wherein the system further comprises a suction device that is connectable to the outlet opening.

The system may further comprise a monitor for showing an image captured by an image capturing means arranged at the distal tip unit.

The present disclosure may also relate to the following aspects, wherein each aspect of the following aspects may be independently and arbitrarily combined with any one of the above mentioned aspects and the claims:

1. An endoscope comprising: a proximal endoscope handle; a distal tip unit configured to be inserted into a patient's body cavity; an endoscope shaft connecting the endoscope handle and the distal tip unit; a working channel provided in the endoscope shaft and extending from the endoscope handle towards the distal tip unit; and a suction valve configured to control a suction through the working channel and having a valve closed state and a valve open state; the suction valve comprising: a housing having an inlet opening connected to the working channel and an outlet opening; and a piston unit inserted in the housing, the piston unit comprising: a movable piston; a button attached to the piston; a fixation ring arranged stationary in the housing; and a spring arranged and acting between the fixation ring and the button or piston; the button being a one-piece or integral part having an integrated sealing portion, the integrated sealing portion contacting the housing and providing a sealing between the button and the housing in the valve open state.
2. Endoscope according to aspect 1, wherein the button comprises a first button portion made of a first material and a second button portion made of a second material, wherein the first material is different from the second material.
3. Endoscope according to aspect 2, wherein the first material and the second material are both polymer materials and the first material is a rigid polymer material and the second material is a flexible polymer material.
4. Endoscope according to aspect 2 or 3, wherein the second button portion comprises the integrated sealing portion.
5. Endoscope according to any of aspects 2 to 4, wherein the second button portion comprises the integrated sealing portion, an inner circular portion and an elongated portion, the elongated portion extending radially outwardly from the inner circular portion.
6. Endoscope according to aspect 5, wherein the inner circular portion and the elongated portion are visible from outside in an assembled state of the suction valve, and the integrated sealing portion is provided on an inner side of the button and is not visible from outside in the assembled state of the suction valve.
7. Endoscope according to any of aspects 2 to 6, wherein a color of the first material is different from a color of the second material.
8. Endoscope according to aspect 1, wherein the button comprises a round button cover portion and a cylindrical button shell portion extending from the button cover portion.
9. Endoscope according to aspect 8, wherein the button cover portion comprises an outer circular portion, an inner circular portion and an elongated portion, the elongated portion extending radially outwardly from the inner circular portion and thus interrupting the outer circular portion, wherein the outer circular portion is made of a first material, the inner circular portion and the elongated portion are made of a second material, and a color of the first material is different from a color of the second material.

Endoscope according to aspect 8 or 9, wherein the button has an inwardly protruding portion, the inwardly protruding portion protruding inwardly from the button cover portion and being configured to snap onto the piston.

11. Endoscope according to any of aspects 8 to 10, wherein the button is provided with at least one leakage slit, preferably several leakage slits, allowing leakage flow in the valve closed state, the at least one leakage slit being provided in the cylindrical button shell portion.
12. Endoscope according to any of aspects 1 to 11, wherein the button is a multi-component injection molded part.
13. System comprising an endoscope according to any of aspects 1 to 12, wherein the system further comprises a suction device connectable to the outlet opening.
14. System according to aspect 13, wherein the system further comprises a monitor for showing an image captured by an image capturing means arranged at the distal tip unit.

BRIEF DESCRIPTION OF FIGURES

The disclosure is explained in more detail below using preferred embodiments and referring to the accompanying figures.

The figures are schematic in nature and serve only to understand the disclosure. Identical elements are marked with the same reference signs. The features of the different embodiments can be interchanged among each other.

DETAILED DESCRIPTION OF PREFERRED EMBODIMENTS

Figure 1:
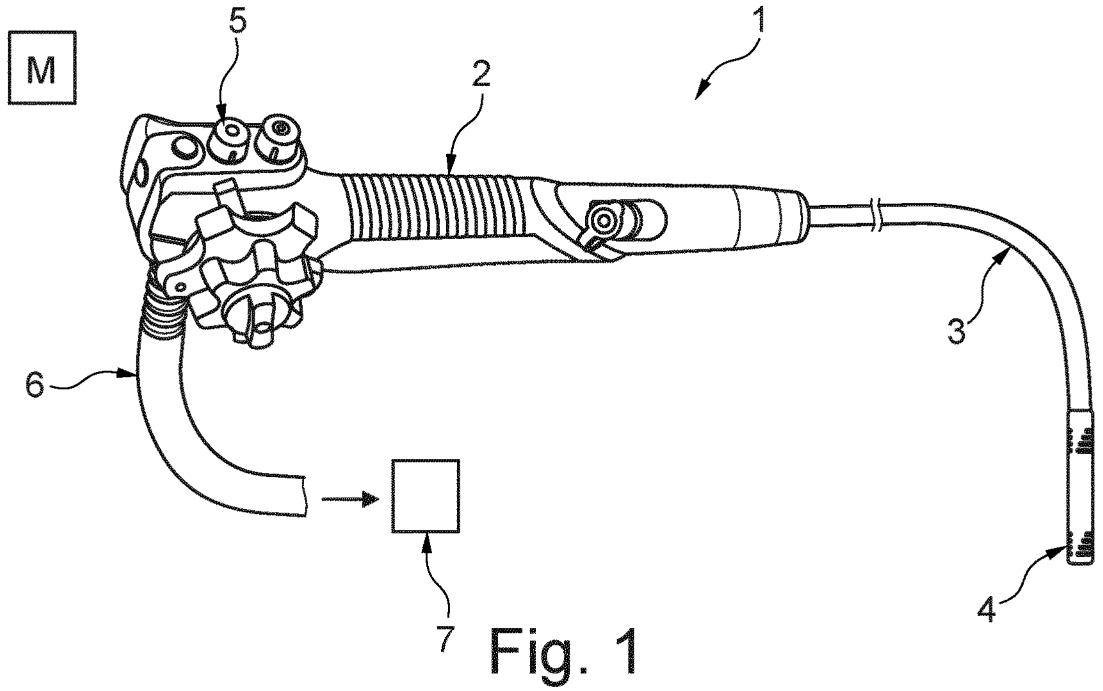
FIG. 1 is a perspective view of an endoscope comprising a suction valve.

In FIG. 1, an endoscope 1 is shown. The endoscope 1 is preferably configured as a single use endoscope and comprises a handle 2 designed to be held by a user. An at least partially flexible endoscope shaft 3 extends from the handle 2 to a distal tip unit 4, which is intended to be inserted into a patient's body cavity. The endoscope shaft 3 is (internally) provided with a working channel (not visible in the figures).

At the distal tip unit 4, image capturing means such as a miniature video camera and illuminating means such as light-emitting diodes or fibre optic light guides connected to a proximal source of light are arranged/installed, such that the patient's body cavity can be illuminated and inspected. An image captured by the image capturing means can be shown on a monitor M. The monitor M is provided separately from and connected with the endoscope 1. Further, the endoscope 1 is provided with the internal working channel which is formed within the endoscope shaft 3 and which is configured to guide a surgical instrument from the proximal endoscope handle 2 into the patient's body cavity. The user is therefore able to perform endoscopic examinations within the patient's body cavity.

A suction valve 5 is provided at the handle 2. Here, the suction valve 5 is inserted into the handle 2. One end of a suction tube 6 is connected to the suction valve 5. The other end of the suction tube 6 is connected to a suction device (a suction pump/vacuum pump) 7 that exerts a suction effect on the working channel via the suction valve 5.

Figure 2:
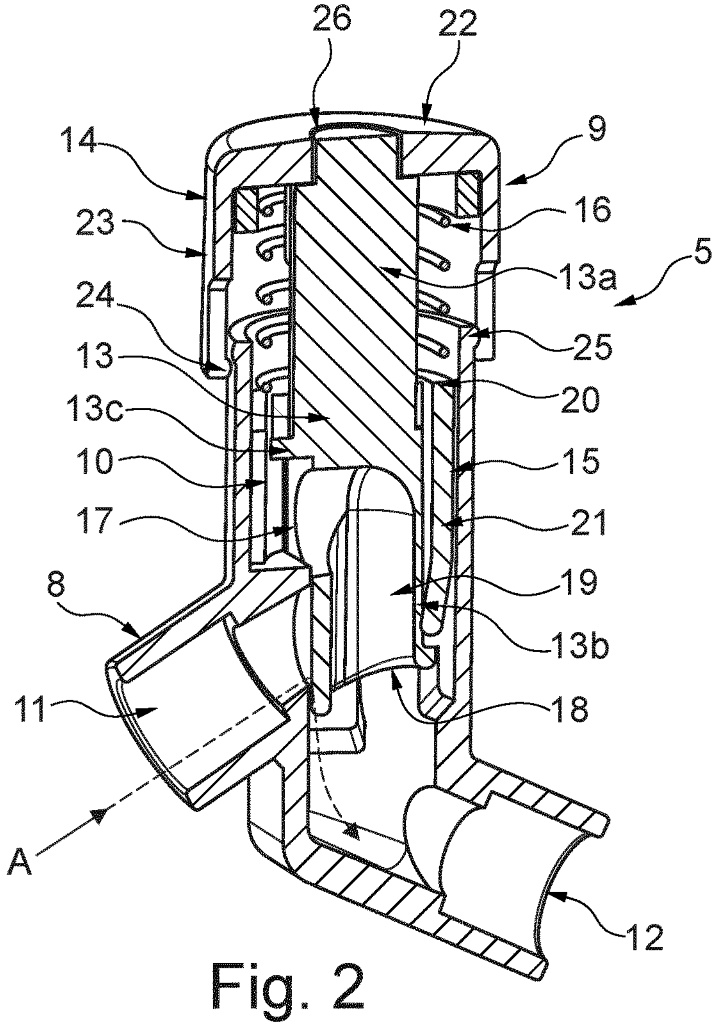
FIG. 2 is a longitudinal sectional view of a suction valve in a valve closed state.

FIG. 2 shows a longitudinal sectional view of a suction valve 5 according to a first preferred embodiment. The suction valve 5 comprises a housing 8 and a piston unit 9. In FIG. 2, the piston unit 9 is illustrated in a case in which it is accommodated in/inserted into the housing 8. The housing 8 is essentially formed as a hollow cylinder whose cavity defines an internal guiding channel 10. The piston unit 9 is inserted into an open (upper) end of the housing 8. An outer shell surface of the housing 8 is interrupted by a first protruding pipe portion which is angled, especially in an obtuse angle, relative to a length axis of the housing 8. The first protruding pipe portion defines the inlet opening 11 of the housing 8. The outer shell surface of the housing 8 is further interrupted by a second protruding pipe portion which is angled, especially in an obtuse angle, relative to the length axis of the housing 8. The first protruding pipe portion and the second protruding pipe portion are essentially diametrically opposed to each other and the first protruding pipe portion is arranged above the second protruding pipe portion in a length/axial direction of the housing 8. The second protruding pipe portion defines the outlet opening 12 of the housing 8.

The piston unit 9 accommodated in the internal guiding channel 10 comprises a piston 13, a button 14 that is fixed to the piston 13, a fixation ring 15 that is arranged immovably/stationary inside the housing 8 and a spring 16 that is positioned between the button 14 and the fixation ring 15. Although the spring 16 is positioned between the button 14 and the fixation ring 15 according to FIG. 2 it is to be understood that the spring 16 may alternatively be arranged and act between the piston 13 and the fixation ring 15. In other words, it is only necessary that the spring 16 is arranged and acts between the assembly consisting of the piston 13 and the button 14, and the fixation ring 15. The internal guiding channel 10 is configured to accommodate the piston unit 9 such that the piston 13 is movable/slidable inside the internal guiding channel 10.

The piston 13 includes a cylindrically shaped first (upper) piston portion **13*a* and a second (lower) piston portion 13*b* both merging into a transition area 13*c* arranged between the first piston portion 13*a* and the second piston portion 13*b*. The first piston portion 13*a*, the second piston portion 13*b* and the transition area 13*c*** are integrally connected with each other.

The transition area **13*c* is provided with a radially outwardly protruding rim portion that is arranged between the first piston portion 13*a* and the second piston portion 13*b*. The radially outwardly protruding rim portion is urged against the fixation ring 15 by the spring 16** in the valve closed state.

The second piston portion **13*b* is provided with a cavity that interrupts a shell surface of the second piston portion 13*b* defining a first (side) opening 17 of the piston 13 and that interrupts a free end surface (bottom side) of the second piston portion 13*b* defining a second (bottom) opening 18 of the piston 13. The cavity between the first opening 17 and the second opening 18 defines a flow channel 19 of the piston 13 that allows a fluid flow between the first opening 17 and the second opening 18. The second opening 18 of the piston 13 is in fluid connection with the outlet opening 12 of the housing 8**.

The fixation ring 15 comprises a ring-shaped/annular/circular ring-like portion 20 (afterwards simply called "ring-shaped portion 20") from which a protruding portion 21 is extending. The protruding portion 21 contacts the second piston portion **13*b*. The ring-shaped portion 20 encircles/encloses/surrounds the first piston portion 13*a*. The piston 13 is movable relative to the ring-shaped portion 20 of the fixation ring 15. When the piston unit 9 is accommodated within the housing 8, the fixation ring 15 is preferably fixed within/to the housing 8**.

The protruding portion 21 of the fixation ring 15 is designed as a spring-type finger in FIG. 2, and urges/presses the piston 13, in particular the second piston portion **13*b*** towards the inlet opening 11 by a spring force. This spring-type finger is configured as a leaf spring.

In particular, the protruding portion 21 has a first (upper) portion extending essentially in an axial direction of the suction valve (along the piston 13) and a second (lower) portion being inclined with respect to the first (upper) portion towards the piston 13 (towards the second piston portion 13*b*) and contacting/pressing onto the piston 13 with a free end of the protruding portion 21.

The button 14 encompasses and covers the open end of the housing 8. For this purpose, the button 14 is formed like a hollow cylinder. The button 14 has a round button cover portion 22 and a cylindrical button shell portion 23 extending from the button cover portion 22. The button 14 is open at a free end that is opposed to the button cover portion 22. Hence, the button 14 defines an internal button cavity that is configured to accommodate the housing 8. The button 14 and the housing 8 are connectable with each other in a snap fit engaging manner. For this purpose, the open end of the button 14 is provided with an inwardly extending first snap-fit rim 24 and the (upper) end of the housing 8 that may be brought in contact with the button 14 is provided with an outwardly extending second snap-fit rim 25. When the piston unit 9 is connected to the housing 8, the first and the second snap-fit rims 24, 25 work together in such way that they limit a longitudinal movement of the piston 13 (unit) relative to the housing 8.

At its centre, the button cover portion 22 is provided with a circular hole 26 of such a size that it can accommodate the free (upper) end of the first piston portion 13*a*. In this way, the button 14 is fixable to the piston 13 such that the piston 13 is movable together with the button 14.

The spring 16 is interposed between the ring-shaped portion 20 of the fixation ring 15 and the button 14. In FIG. 2, one end of the spring 16 contacts the ring-shaped portion 20 and the other end of the spring 16 contacts an inner surface of the button cover portion 22. The elastic force of the spring 16 is at least so large that the piston 13 is held in such a position relative to the housing 8 that a shell surface of the second piston portion 13*b* covers/seals the inlet opening 11 of the housing 8 in the valve closed state, as can be seen in FIG. 2. Hence, FIG. 2 shows a valve closed state, in which the piston 13 seals the inlet opening 11 against a fluid flow through the suction valve 5.

In FIG. 2, arrow A indicates a residual suction that enters the suction valve over the inlet opening in the valve closed state. This residual suction occurs when the suction device is running in the valve closed state and the inlet opening is not completely sealed by the second piston portion 13*b*. The object of the present disclosure is to reduce the residual suction as much as possible or to even eliminate the residual suction.

Figure 3:
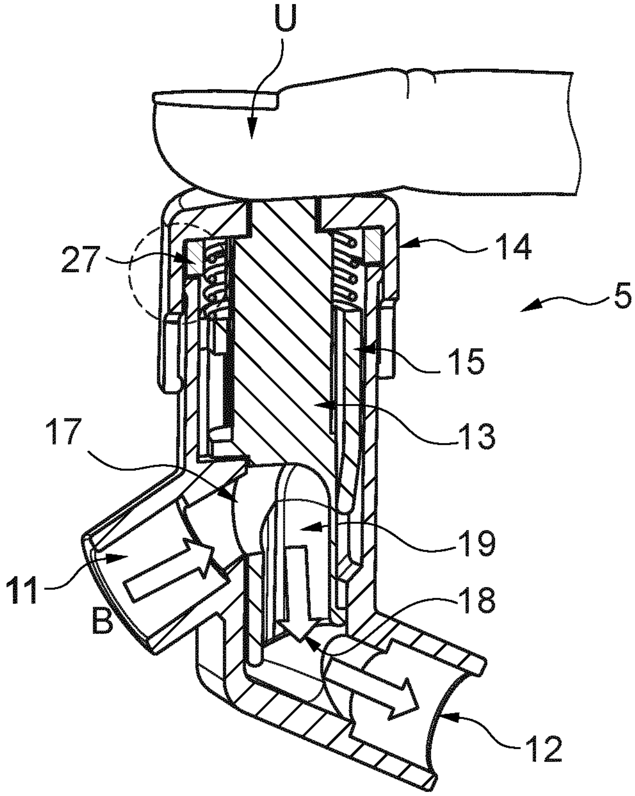
FIG. 3 is a longitudinal sectional view of the suction valve of FIG. 2 in a valve open state.

FIG. 3 shows a longitudinal sectional view of the suction valve 5 of FIG. 2 in the valve open state. In this case, the inlet opening 11 is in direct contact/is flush with the first opening 17 such that a fluid flow, indicated by an arrow B, from the inlet opening 11 through the flow channel 19 of the piston 13 and to the outlet opening 12 is allowed. Hence, in the valve open state, fluid, like air, water or mucus, from the patient's body cavity can be suctioned/drawn out of the working channel by the suction device 7. This improves the sight and hence the working accuracy of a user of the endoscope.

Advantageously, the inlet opening 11 and the first opening 17 have the same diameter (at least where the inlet opening 11 and the first opening 17 are in flush contact) to prohibit fluid losses in the valve open state.

The suction valve 5 can be transitioned from the valve closed state to the valve open state in the following way:

First, a user, indicated by U, can manually press (with his finger) the button 14 towards the housing 8 (pressing force acting in a length direction of the suction valve 5). The pressing force of the user U must at least be so great that the elastic force of the spring 16 is overcome, in order to compress the spring 16. Associated with this, the button 14 moves (downwards) together with the piston 13. In this way, the piston 13 is moved/slided downwards inside the internal guiding channel 10 of the housing 8 until the outwardly protruding rim portion in the transition area 13*c* of the piston 13 contacts a stop provided inside the housing 8/the internal guiding channel 10. In this valve open state the first opening 17 and the inlet opening 11 are in flush contact with each other. Moreover, a sealing element 27 provided on an inner side of the button cover portion 22 contacts the (upper) free end of the housing 8. In the valve open state, the sealing element 27 seals the suction valve 5 against suctioning/drawing in air from the surroundings. The sealing element 27 is a separate part which may be fixed/attached, e.g. bonded/glued to the inner side of the button cover portion 22.

When the suction valve 5 shall again be transferred from the valve open state to the valve closed state, the user U simply has to stop pressing onto the button 14 (e.g. by simply releasing his finger). In this case, the spring 16 relaxes and its elastic force moves the button 14 and the piston 13 in a direction away from the housing 8 (outwardly) back into the valve closed state.

Figure 4:
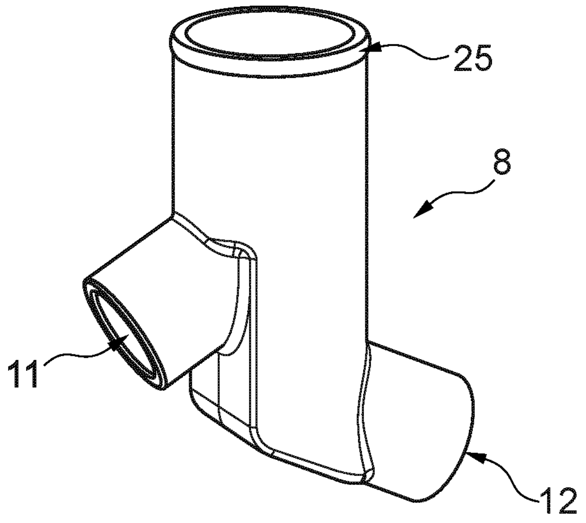
FIG. 4 is a perspective view of a housing.

FIG. 4 is a perspective view of the housing 8. Here, the exact shape of the housing 8 can be seen in detail. The housing 8 is formed essentially like a hollow cylinder. The (upper) end of the housing 8 that can be brought in contact with the button 14 is open and round/circular and defines the second snap-fit rim 25. The housing 8 has in total three openings. In addition to the opening at the upper end there is provided the inlet opening 11 and the outlet opening 12. Both the inlet opening 11 and the outlet opening 12 are formed as protruding pipe portions.

Figure 5:
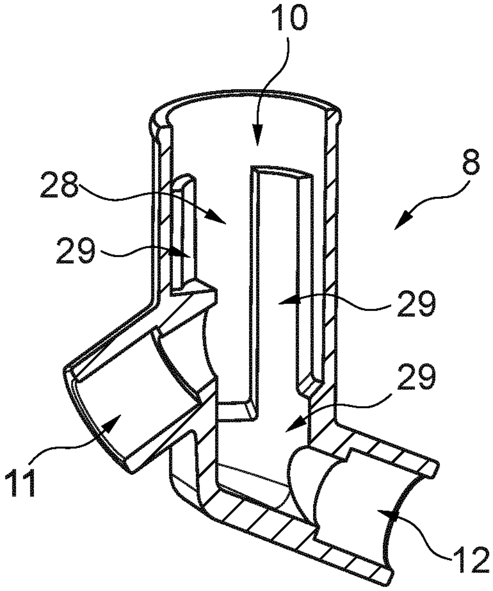
FIG. 5 is a longitudinal sectional view of the housing.

FIG. 5 is a longitudinal section view of the housing 8. Here, the formation of the internal guiding channel 10 can be seen in detail. The internal guiding channel 10 is provided with at least one groove 28 that extends in a length direction of the housing 8 along its inner surface. The at least one groove 28 is formed by adjacent protruding guiding portions 29 protruding inwardly from an internal wall of the housing 8. The groove 28 allows a leakage flow through the suction valve 5, especially through the internal guiding channel 10 and the flow channel 19, in the valve closed state.

Figure 6:
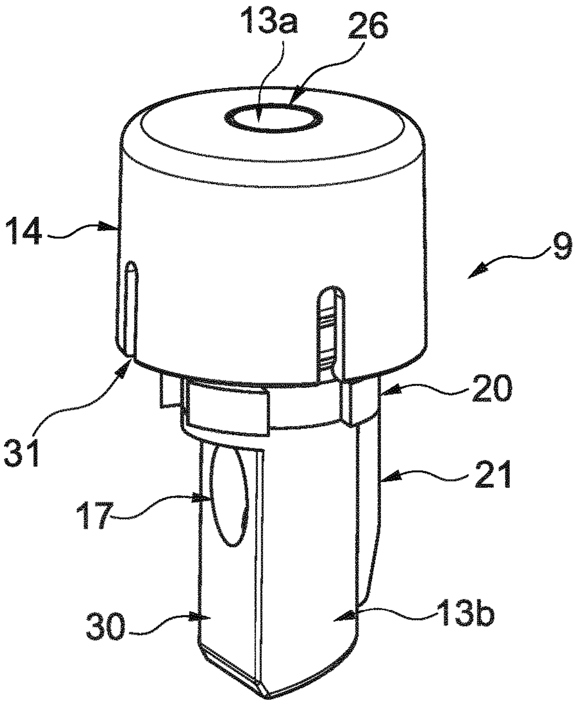
FIG. 6 is a perspective view of a piston unit.

FIG. 6 is a perspective view of the piston unit 9. It can be seen that the second piston portion 13*b* of the piston 13 is a cylinder whose shell surface is interrupted by a planar surface 30 that extends in a length direction of the piston 13. The planar surface 30 is configured to contact the inlet opening 11 of the housing 8 and is provided with the first 30 opening 17 which is flush with the inlet opening 11 in the valve open state. Preferably, the internal guiding surface 10 (the inner shell surface of the housing 8) is provided with a correspondingly flat surface at a position/an area around/adjacent the inlet opening 11.

Moreover, it can be seen from FIG. 6, that the outer shell surface of the ring-shaped portion 20 of the fixation ring 15 is not continuous but interrupted by a plurality of (equidistantly separated) recesses. These recesses are configured to accommodate the protruding guiding portions 29 of the internal guiding channel 10. The protruding guiding portions

29 fit into the recesses of the ring-shaped portion 20 such that the fixation ring 15 can be fixed to the housing 8.

Furthermore, it can be seen from FIG. 6, that the cylindrical button shell portion 23 is provided with at least one, here with a plurality of (circumferentially equidistantly arranged) leakage slits 31 extending lengthwise from the open end of the button 14. The leakage slits 31 have an elongated slotted hole shape and allow air from the surroundings to be sucked into the suction valve 5 in the valve closed state. When the suction device 7 is running in the valve closed state, a leakage flow of air through the internal guiding channel 10 and through the flow channel 19 is basically desired. This has the purpose of avoiding a built-up of a vacuum in the valve closed state which would result in an undesirable rapid increase in suction flow when the suction valve 5 is transferred from the valve closed state to the valve open state. A rapid increase in suction flow could lead to damages to the tissue of the patient's body cavity. Typically, a slower increase in suction flow is desired when the suction device 5 is transferred to the valve open state. With the leakage flow entering the suction valve 5 over the leakage slits 31 the pressure in the suction valve 5 is closer to the atmospheric pressure and therefore the (residual) suction in the valve closed state can be reduced.

Figure 7:
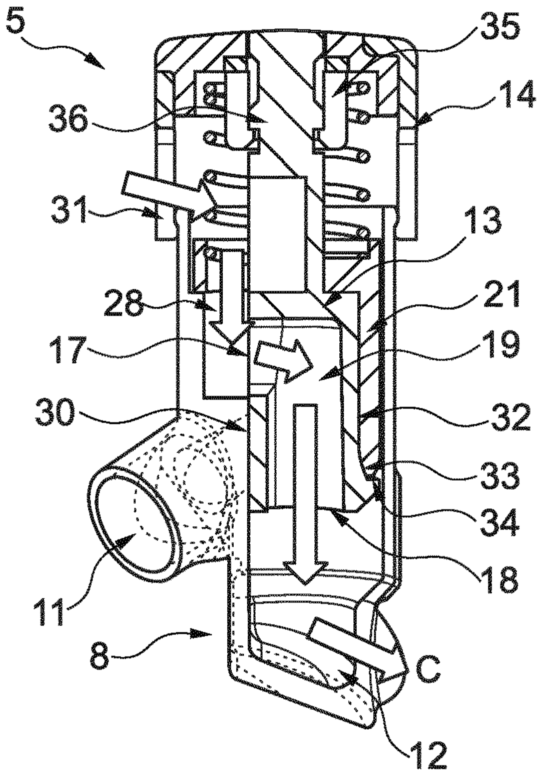
FIG. 7 is a longitudinal sectional view of a suction valve in a valve closed state indicating a leakage flow.

FIG. 7 is a longitudinal sectional view of a suction valve 5 according to a second preferred embodiment in the valve closed state. In FIG. 7 a leakage flow entering over the leakage slits 31 into the button 14 is indicated by means of arrow C. Here, it can be seen that the leakage flow first flows along the groove 28 of the internal guiding channel 10 and then enters the flow channel 19 of the piston 13 via the first opening 17. The leakage flow exits the piston 13 via the second opening 18 and then exits the suction valve 5 via the outlet opening 12.

As already described above, in the valve closed state, the piston 13, especially the planar surface 30 of the piston 13 contacting the correspondingly flat surface of the internal guiding channel 10, seals the inlet opening 11. It is an aim of this disclosure that the residual suction entering the suction valve 5 over the inlet opening 11 shall be reduced or even eliminated in the valve closed state. For this purpose an effective sealing between (the planar surface 30 of) the piston 13 and the inlet opening 11 is necessary. Against this background, in this disclosure, the fixation ring 15 is configured to urge the piston 13 against the inlet opening 11. FIG. 7 shows a second embodiment that allows the fixation ring 15 to exert an urging effect on the piston 13.

FIG. 7 shows a piston 13 of the suction valve 5 wherein the second piston portion 13*b* has an axially extending shell portion 32 (afterwards simply called "shell portion") and an inclined portion 33 integrally connected to/formed at an end of the shell portion 32. The inclined portion 33 is at such position that the protruding portion 21 of the fixation ring 15 can contact this inclined portion 33 such as to apply a pressing force onto the piston 13 towards the inlet opening 11. In the inclined portion 33 an outer diameter of the piston 13 gradually/continuously/linearly increases (starting) from the shell portion 32. The protruding portion 21 of the fixation ring 15 is formed like a wedge and engages at least with the inclined portion 33 in the valve closed state, thus urging the inclined portion 33 towards the inlet opening 11 of the housing 8.

In this case, the second piston portion 13*b* is not just provided with an inclined portion 33 to allow the urging effect, but the end of the second piston portion 13*b* is further provided with a radially outwardly protruding flange portion 34 (afterwards simply called "flange portion"). The inclined portion 33 is arranged between the shell portion 32 and the flange portion 34. The inclined portion 33 and the flange portion 34 form together a holding portion. This holding portion can engage with the wedge-like protruding portion 21 of the fixation ring 15. The flange portion 34 may accommodate the wedge-like protruding portion 21 of the fixation ring 15. In the valve closed state, the wedge-like protruding portion 21 contacts the inclined portion 33 and may be held by the flange portion 34. As the inclined portion 33 extends outwardly starting from the shell portion 32, in the valve-closed state, the wedge-like protruding portion 21 of the fixation ring 15 exerts a pressing force onto the inclined portion 33 which is directed towards the inlet opening 11. Hence, the piston 13 is urged/pressed by (the wedge-like protruding portion 21 of) the fixation ring 15 against the inlet opening 11 and hence effectively seals the inlet opening 11 against an undesired residual suction. Thus, in the valve closed state, only a desired leakage flow C entering over the leakage slits 31 streams through the suction valve 5.

As already described above, at least two embodiments are imaginable to enable an urging effect of the fixation ring 15 onto the piston 13 towards the inlet opening 11. The first embodiment is that the protruding portion 21 of the fixation ring 15 is designed as a spring-type finger, urging the piston 13 towards the inlet opening by a spring force, as can be seen in FIG. 2 and FIG. 3.

Moreover, in the embodiment shown in FIG. 7 (as well as in FIG. 8), a special fixing mechanism between the button 14 and the piston 13 is visible. Here, the button 14 has a first holding arrangement 35 which comprises an inwardly protruding portion, the inwardly protruding portion protruding inwardly from the button cover portion 22 and being configured to snap onto the piston 13. The first piston portion 13*a* is provided with a second holding arrangement 36. The second holding arrangement 36 of the piston 13 is configured to be complementary to and to be engaged with the first holding arrangement of the button 14. The interaction of the first and second holding arrangements 35, 36 allows a snap-fit arrangement between the button 14 and the piston 13.

Figure 8:
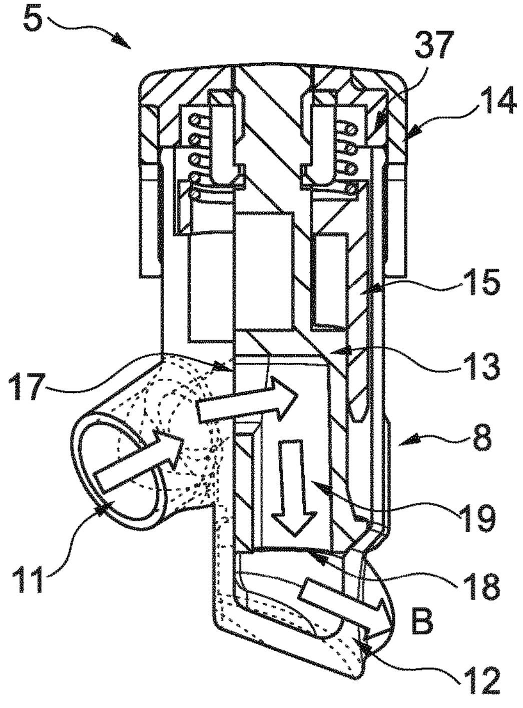
FIG. 8 is a longitudinal sectional view of the suction valve of FIG. 7 in a valve open state indicating a suction flow.

FIG. 8 is a longitudinal sectional view of the suction valve 5 of FIG. 7 in the valve open state. Here, due to the valve open state, a fluid/suction flow, indicated by arrow B, between the inlet opening 11 and the outlet opening 12 is allowed. Compared to FIG. 7, the button 14 was pushed (downwards) towards the housing 8 such that the piston 13 is in such height that its first opening 17 is in flush contact with the inlet opening 11 of the housing 8. Furthermore, it can be seen that the fixation ring 15 has the same position in the valve open state as in the valve closed state as (the ring-shaped portion 20 of) the fixation ring is fixed to the housing 8. Therefore, in the valve open state the wedge-like protruding portion 21 of the fixation ring 15 is not in contact with the inclined portion 33 of the piston 13 and thus does not urge the piston 13 towards the inlet opening 11.

In the second embodiment shown in FIG. 7 and FIG. 8 a special preferred embodiment of the button 14 is realized. It is to be understood however that this special preferred embodiment of the button may also be applied for the first embodiment shown in FIG. 2 and FIG. 3. In other words the configuration of the button 14 in the second embodiment shown in FIG. 7 and FIG. 8 may also be applied for the first embodiment shown in FIG. 2 and FIG. 3.

As already discussed above, in the first embodiment shown in FIG. 2 and FIG. 3 a separate sealing element 27 is attached to the inner side of the button cover portion 22.

According to a special preferred embodiment the button 14 may however be integrally provided with a sealing. In particular the button 14 may be a one-piece or integral part having an integrated sealing portion 37 replacing the separate sealing element 27. As can be seen in particular in FIG. 8 the integrated sealing portion 37 contacts the (upper free end of the) housing 8 and provides a sealing between the button 14 and the housing 8 in the valve open state. The integrated sealing portion 37 seals the suction valve 5 in the valve open state against undesired suction of air from the surroundings.

Figure 9:
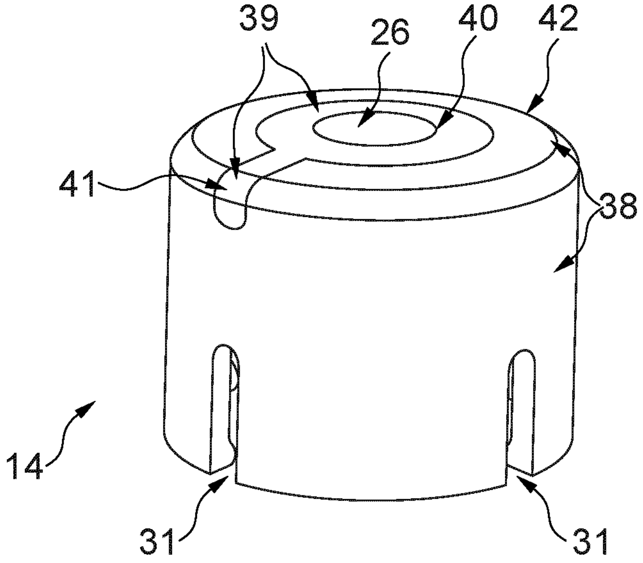
FIG. 9 is a perspective view of a preferred embodiment of a button comprising a first button portion and a second button portion.

FIG. 9 is a perspective view of the button 14 according to the special preferred embodiment. As can be seen, the button 14 comprises a first button portion 38 and a second button portion 39. Preferably, the first button portion 38 is made of a first material and the second button portion 39 is made of a second material. The first material may have a higher modulus of elasticity than the second material (the first material is more rigid than the second material).

The second button portion 39 (made of the second material) comprises the integrated sealing portion 37, an inner circular portion 40 and an elongated portion 41. The inner circular portion 40 is at its center provided with the circular hole 26. The elongated portion 41 extends radially outwardly from the inner circular portion 40. The first button portion 38 is visually distinguishable from the second button portion 39. Preferably, the second button portion 39 is of another colour than the first button portion 38, especially the second button portion 39 is red as this colour indicates a user that this valve is used to control suction of the endoscope, whereas the first button portion 38 is of another colour than red. When the integrated sealing portion 37 is provided integrally with the button 14, no additional and/or separate sealing is necessary for such a suction valve 5. Hence, the assembly of such suction valve 5 can be simplified.

In FIG. 9, it can be seen, that the button cover portion 22 comprises the inner circular portion 40 made of the second material and an outer circular portion 42 made of the first material. Moreover, the button cover portion 22 comprises the elongated portion 41. The inner circular portion 40 is arranged at the centre of the button cover portion 22 and is encircled by the outer circular portion 42 of the first material.

In FIG. 9, also one single elongated portion 41 can be seen. The elongated portion 41 is a portion that extends from the inner circular portion 40 in a radial direction of the button 14 towards an outer edge of the button 14 at which the button cover portion 22 merges into the outer cylindrical button shell portion 23. The elongated portion 41 can be used as a marking/a visual marker to show a user the correct orientation of the button 14 relative to the housing 8 or relative to the piston 13, when mounting the piston unit 9 to the housing 8 or when mounting the button 14 to the piston 13. For this purpose, the housing 8 or the piston 13 may have a corresponding marking, which is not shown in the figures. In this way, the button 14 indicates the correct orientation of the button 14 to an assembler/user.

By providing the integrated sealing portion 37 in the button 14, the assembly process is eased as fewer components need to be handled. By providing a visual marker on the external surface of the button 14, the assembly process is eased as the assembler can readily infer the correct orientation of the button 14 for assembly with the remaining components of the valve. By providing a coloured external surface, the use of the button 14 is improved since the user can easily determine the function of the (suction) valve as the red colour is commonly used to indicate a suction function.

Figure 10:
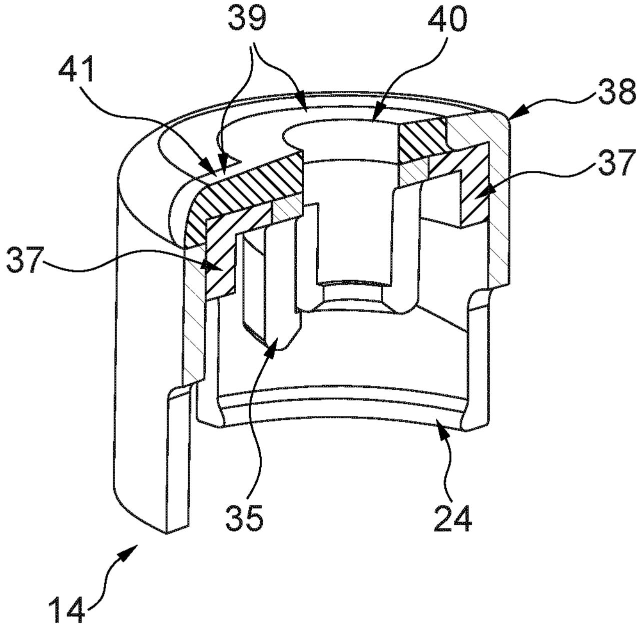
FIG. 10 is a longitudinal sectional view of the button of FIG. 9 comprising the first button portion and the second button portion.

In FIG. 10, a longitudinal sectional view of the button 14 according to the special embodiment can be seen. Here, the second button portion 39 is completely visible. It is to be understood that although different hatchings are used for different portions (inner circular portion 40, elongated portion 41, sealing portion 37) of the second button portion 39 and for different portions of the first button portion 38 in FIG. 10, the second button portion 39 is an integral, one-material portion and the entire button is an integral, one-piece and multi-material part. The integrated sealing portion 37 is arranged inside of the button 14 (on an inner side) and has an L-shaped cross-section, wherein a first leg of the L extends in a radial direction of the button 14 and a second leg of the L extends in a longitudinal direction of the button 14. An end of the second leg provides a sealing surface and is in contact with the housing 8 (in particular with the annular upper rim of the housing 8) in the valve open state. In this way, the integrated sealing portion 37 seals the suction valve 5 against undesired suction of air from the surroundings in the valve open state.

Furthermore, it can be seen in FIG. 10 that according to the special embodiment of the button 14, the first holding arrangement 35 extends towards the housing 8 from an inner surface of the inner circular portion 40. The first holding arrangement 35 may be made of the first material.

The first and the second materials of the button 14 are preferably a first and a second (polymer) material. The first material may be a rigid polymer, e.g. acrylonitrile-butadiene-styrene (ABS) or polycarbonate (PC), which is used for the first button portion 38. The second material may be a flexible polymer able to form a sealing, such as thermoplastic polyurethane (TPU) or silicone, which is used for the second button portion 39. The button 14 may be manufactured using a multi (two)-component injection molding process.

The invention claimed is:

1. An endoscope comprising:

a handle;

a distal tip configured to be inserted into a patient's body cavity;

an endoscope shaft connecting the handle and the distal tip;

a working channel extending from the handle through the endoscope shaft towards the distal tip; and a suction valve configured to control a suction through the working channel and having a valve closed state and a valve open state, the suction valve comprising:

a housing including an internal guiding channel having a longitudinal centerline, an inlet opening connected to the working channel and an outlet opening, the inlet opening being positioned laterally from the internal guiding channel;

a piston unit inserted in the housing, the piston unit comprising:

a piston configured to translate longitudinally in the internal guiding channel, the piston including an upper piston portion and a lower piston portion, the lower piston portion including a first side opening fluidly coupled with the inlet opening of the housing in the valve open state;

a button attached to the upper piston portion;

a fixation ring arranged stationary in the housing and including an upper portion and a protruding portion extending longitudinally away from the upper portion; and a spring arranged and acting between the fixation ring and the button or the piston;

the protruding portion of the fixation ring cooperating with the lower piston portion as the valve transitions from the valve open state to the valve closed state to generate a lateral force urging the lower piston portion towards the inlet opening of the housing in the valve closed state, wherein said cooperating includes sliding engagement of a surface of the lower piston portion of the piston that is oblique relative to a longitudinal direction against a surface of the protruding portion such that the longitudinal translation of the piston produces the lateral force.

2. The endoscope of claim 1, wherein the fixation ring is configured to assist in sealing the piston in the valve closed state.

3. The endoscope of claim 1, wherein at least an end portion of the protruding portion is brought into contact with the piston at least in the valve closed state to urge the piston laterally towards the inlet opening of the housing.

4. The endoscope of claim 3, wherein the protruding portion is arranged diametrically opposed with respect to the inlet opening of the housing.

5. The endoscope of claim 4, wherein the piston comprises a transition area between the upper piston portion and the lower piston portion.

6. The endoscope of claim 5, wherein the piston has a radially outwardly protruding rim portion in the transition area, the radially outwardly protruding rim portion being urged against the fixation ring by the spring in the valve closed state.

7. An endoscope comprising:

a handle;

a distal tip configured to be inserted into a patient's body cavity;

an endoscope shaft connecting the handle and the distal tip;

a working channel extending from the handle through the endoscope shaft towards the distal tip and a suction valve configured to control a suction through the working channel and having a valve closed state and a valve open state, the suction valve comprising:

a housing having an inlet opening connected to the working channel and an outlet opening;

a piston unit inserted in the housing, the piston unit comprising:

a piston;

a button attached to the piston;

a fixation ring arranged stationary in the housing and including an upper portion and a protruding portion extending longitudinally away from the upper portion; and a spring arranged and acting between the fixation ring and the button or the piston;

wherein the piston comprises a first piston portion, a second piston portion and a transition area between the first piston portion and the second piston portion, wherein the second piston portion has an axially extending shell portion and an inclined portion formed at an end of the axially extending shell portion, wherein in the inclined portion an outer radius of the piston continuously increases from the axially extending shell portion, and wherein the protruding portion of the fixation ring is formed like a wedge and engages at least with the inclined portion of the piston in the valve closed state to urge the inclined portion of the piston towards the inlet opening of the housing.

8. The endoscope of claim 7, wherein an obtuse angle is formed between the axially extending shell portion and the inclined portion.

9. The endoscope of claim 7, wherein the second piston portion has a radially outwardly protruding flange portion at an end of the second piston portion, wherein the inclined portion is arranged between the axially extending shell portion and the radially outwardly protruding flange portion, and wherein in the inclined portion an outer radius of the piston continuously increases from the axially extending shell portion to the radially outwardly protruding flange portion.

10. An endoscope comprising:

a handle;

a distal tip configured to be inserted into a patient's body cavity;

an endoscope shaft connecting the handle and the distal tip;

a working channel extending from the handle through the endoscope shaft towards the distal tip; and a suction valve configured to control a suction through the working channel and having a valve closed state and a valve open state, the suction valve comprising:

a housing having an inlet opening connected to the working channel and an outlet opening;

a piston unit inserted in the housing, the piston unit comprising:

a piston;

a button attached to the piston;

a fixation ring arranged stationary in the housing; and a spring arranged and acting between the fixation ring and the button or the piston;

wherein the fixation ring has a ring-shaped portion and a protruding portion extending axially away from the ring-shaped portion and along the piston, and wherein an end portion of the protruding portion is designed as a spring-type finger configured to contact the piston, at least in the valve closed state, to urge the piston towards the inlet opening of the housing by a spring force.

11. The endoscope of claim 10, wherein the spring-type finger is configured as a leaf spring.

12. An endoscope comprising:

a handle;

a distal tip configured to be inserted into a patient's body cavity;

an endoscope shaft connecting the handle and the distal tip;

a working channel extending from the handle through the endoscope shaft towards the distal tip; and a suction valve configured to control a suction through the working channel and having a valve closed state and a valve open state, the suction valve comprising:

a housing having an inlet opening connected to the working channel and an outlet opening;

a piston unit inserted in the housing, the piston unit comprising:

a piston including a first piston portion, a second piston portion and a transition area between the first piston portion and the second piston portion, the second piston portion having an axially extending shell portion and an inclined portion formed at an end of the axially extending shell portion, in the inclined portion an outer radius of the piston continuously increasing from the axially extending shell portion;

a button attached to the piston;

a fixation ring arranged stationary in the housing, the fixation ring having a ring-shaped portion and a protruding portion extending axially away from the ring-shaped portion and along the piston; and a spring arranged and acting between the fixation ring and the button or the piston;

wherein an end portion of the protruding portion of the fixation ring is formed like a wedge configured to slidingly engage at least with the inclined portion of the piston in the valve closed state to urge the inclined portion of the piston towards the inlet opening of the housing.

13. The endoscope of claim 12, wherein the piston has a radially outwardly protruding rim portion in the transition area between the first piston portion and the second piston portion, the radially outwardly protruding rim portion being urged against the fixation ring by the spring in the valve closed state.

14. The endoscope of claim 12, wherein the protruding portion extends from the ring-shaped portion towards and along the second piston portion in an axial direction of the piston.

15. The endoscope of claim 12, wherein the second piston portion has a radially outwardly protruding flange portion at an end of the second piston portion, wherein the inclined portion is arranged between the axially extending shell portion and the radially outwardly protruding flange portion, and wherein in the inclined portion an outer radius of the piston continuously increases from the axially extending shell portion to the radially outwardly protruding flange portion.

16. A system comprising:

the endoscope of claim 1, the endoscope comprising a video camera arranged at the distal tip; and a monitor connectable to the endoscope and configured to show video captured by the video camera.

17. A system comprising:

the endoscope of claim 7, the endoscope further comprising a video camera arranged at the distal tip; and a monitor connectable to the endoscope and configured to show video captured by the video camera.

18. A system comprising:

the endoscope of claim 10, the endoscope further comprising a video camera arranged at the distal tip; and a monitor connectable to the endoscope and configured to show video captured by the video camera.

19. A system comprising:

the endoscope of claim 12, the endoscope further comprising a video camera arranged at the distal tip; and a monitor connectable to the endoscope and configured to show video captured by the video camera.

* * * * *